(12) United States Patent
Austen et al.

(10) Patent No.: US 7,022,213 B1
(45) Date of Patent: Apr. 4, 2006

(54) GAS SENSOR AND ITS METHOD OF MANUFACTURE

(75) Inventors: Malcolm Trayton Austen, Middlesex (GB); John Robert Dodgson, Surrey (GB)

(73) Assignee: Invensys Controls UK Limited, (GB)

( * ) Notice: Subject to any disclaimer, the term of this patent is extended or adjusted under 35 U.S.C. 154(b) by 454 days.

(21) Appl. No.: 10/069,209

(22) PCT Filed: Aug. 24, 2000

(86) PCT No.: PCT/GB00/03281

§ 371 (c)(1),
(2), (4) Date: Jun. 3, 2002

(87) PCT Pub. No.: WO01/14868

PCT Pub. Date: Mar. 1, 2001

(30) Foreign Application Priority Data

Aug. 24, 1999 (GB) .................... 9919906

(51) Int. Cl.
*G01N 27/407* (2006.01)
*H01R 4/58* (2006.01)

(52) U.S. Cl. ............... 204/432; 427/296; 439/91; 200/264

(58) Field of Classification Search ........... 427/243, 427/244, 245, 296; 204/431, 432; 439/91; 29/854; 174/84 R; 200/264
See application file for complete search history.

(56) References Cited

U.S. PATENT DOCUMENTS

| 4,132,616 | A | * | 1/1979 | Tantram et al. | ............. 204/415 |
| 4,322,278 | A | * | 3/1982 | Cromer | ............. 204/412 |
| 5,173,166 | A | * | 12/1992 | Tomantschger et al. | .... 204/412 |
| 5,314,605 | A | * | 5/1994 | Matthiessen | ............. 204/415 |
| 5,914,019 | A | * | 6/1999 | Dodgson et al. | ............. 204/415 |

FOREIGN PATENT DOCUMENTS

WO     WO 99/24826    *  5/1999

* cited by examiner

*Primary Examiner*—Kaj K. Olsen
(74) *Attorney, Agent, or Firm*—Andrus, Sceales, Starke & Sawall, LLP

(57) ABSTRACT

The invention relates to a gas sensor and its method of manufacture.

Electrochemical gas sensors usually comprise an external housing, which acts as a reservoir for electrolyte; a wick to keep electrodes wetted with the electrolyte and external electrical terminals, for making electrical contact with the electrodes. Typically a gas permeable/microporous membrane has been used to seal a gas sensor in order to prevent leakage of electrolyte. A problem with existing sensors has been that there was a risk of electrolyte leaking through the membrane around the region where electrical connectors passed therethrough.

The present invention overcomes this by providing a method of urging conductive polymer through the membrane under controlled conditions of heat and pressure, thereby ensuring the integrity of the membrane remains in tact while defining an electrically/conductive pathway therethrough.

23 Claims, 2 Drawing Sheets

GAS SENSOR AND ITS METHOD OF MANUFACTURE

This application is a 35 U.S.C. 371 national stage filing of International Application PCT/GB00/03281, filed on Aug. 24, 2000, which claims priority to Great Britain Application 9919906.9, filed on Aug. 24, 1999.

BACKGROUND OF THE INVENTION

1. Field of the Invention

The present invention relates to a gas sensor, and to its method of manufacture. It relates particularly, but not exclusively, to an electrochemical gas sensor for sensing carbon monoxide (CO) gas.

2. Prior Art

An electrochemical gas sensor for sensing an oxidisible or reducible gas, such as carbon monoxide, usually includes a sensing electrode, a counter electrode and a diffusion barrier. The diffusion barrier allows gas to be sensed, to pass to the sensing electrode. In one type of gas sensor, as described, for example, in the Applicant's copending International Patent Application No. WO-A1-9614576, the sensing and counter electrodes are located on a gas permeable membrane and are in contact with an electrolyte.

In terms of physical construction, electrochemical gas sensors usually comprise an external housing, which acts as a reservoir for electrolyte; a wick, to keep the electrolyte in contact with the electrodes; and external electrical terminals, which make electrical contact with the electrodes.

During operation of the aforementioned gas sensor, an electrochemical reaction occurs at the sensing electrode with the gas to be sensed, and a reaction also occurs with oxygen at the counter electrode. Electric current is carried through the electrolyte by ions produced in these reactions, and the amount of current indicates the concentration of the gas being sensed. A further electrode (the reference electrode) may be employed, for example, in combination with a potentiostat circuit, to maintain a constant potential difference between the sensing electrode and the electrolyte. This increases the stability of operation of the gas sensor. Electrodes are connected to external current sensors via electrical terminals.

External electrical terminals are usually formed from brass or copper pins. Brass and copper both react with the acid electrolyte, and so the gas sensor has to be specially designed so that the pins do not come into contact with the electrolyte. Platinum does not react with acid, and so platinum strips can be used to form an electrical path between the electrodes and external sensors and/or an external electricity supply. However, platinum strips are commonly placed in a seal region between the housing and the gas permeable membrane, and electrolyte can leak from this region. Platinum is also expensive, and so gas sensors having platinum terminals are expensive to manufacture.

Another example of a gas sensor is described in U.S. Pat. No. 5,314,605 (Dragerwerk). The aforementioned US Patent describes a gas permeable region through which holes have been formed. Electrodes pass through the holes. No matter how carefully the region between the periphery of each hole and the electrode is sealed, there is a risk of electrolyte leaking through this seal.

SUMMARY OF THE INVENTION

An aim of the present invention is to provide a gas sensor that is cheaper to manufacture than existing gas sensors.

Another aim of the invention is to provide a gas sensor that is less prone to leaking than existing gas sensors.

According to a first aspect of the present invention there is provided a method of manufacturing a gas sensor having a housing containing a reservoir which in use receives an electrolyte, the method comprising the steps of: impregnating a gas porous membrane with a conductive material, so that said conductive material defines an electrical pathway between an electrical contact on a first surface of the membrane and an electrode on a second surface of the membrane and arranging the gas porous membrane to seal the reservoir.

Thus in accordance with a first aspect of the invention, a simple and reliable means is provided for connecting one or more electrodes, located within a sealed reservoir of the gas sensor, to an electrical pathway outside the sensor; the method avoiding the use of expensive platinum terminals and one which produces a gas sensor which is less prone to leaking.

Preferably the conductive material comprises a conductive polymer and is introduced into the pores of a microporous membrane under conditions of heat and pressure.

The method may also include the step of attaching a wicking means to one or more of the electrodes. The wicking means ensures that each electrode is/are kept in contact with the electrolyte irrespective of the orientation of the sensor once installed. The wicking means may be pressed or sintered to the or each electrode at a temperature of between 300° C. and 370° C., most preferably between 320° C. and 370° C. The exact temperature depends on the nature of the wicking means, the electrode material, and the substrate. Attachment of a wicking means may be performed before any melted conductive polymer is introduced, in which case the wicking means may have at least one aperture therein through which melted polymer can pass to an electrode.

According to a second aspect of the invention there is provided a method of forming an electrical pathway across a microporous membrane having first and second major surfaces; which membrane in use is impervious to liquid and permeable to gas, comprising the steps of; maintaining sufficient heat to melt a conductive material; urging the melted conductive material through pores of the membrane at a first surface by establishing a pressure differential across the surfaces; controlling the heat and pressure differential until the conductive material emerges at the second surface; and allowing the material to cool so as to form a continuous, electrically conductive pathway from the first to the second surface whilst preserving the liquid impermeability and gas permeability characteristics of the membrane.

Preferably the microporous membrane thereby formed is incorporated into an electrochemical cell which may be incorporated into a gas sensor.

Conductive material may be introduced into the substrate via the wicking means, via the electrodes, via the substrate, or via a combination of these.

The conductive material preferably includes conductive polymer. On cooling and solidification of the conductive material, an electrical path is formed between the electrode and the electrical contact or external connection means. Electric current generated in use, at the sensing electrode, may thus pass via the microporous membrane, by way of the conductive polymer to the external connection means, and then to a suitable electronic device (or current source in the case of a test gas generator) where the amount of current generated at the sensing electrode can be measured.

The first and second electrodes are preferably formed from a porous electrically conductive material containing PTFE or similar polymeric binder. Electrodes may also contain particles of catalyst, and optional, additional catalyst support material and material to enhance conductivity.

Electrodes may be formed on the substrate by, for example, screen printing, filtering in selected areas from a suspension placed onto the substrate, by spray coating, ink jet printing, sintering, or any other method suitable for producing a patterned deposition of solid material. Deposition might be of a single material, or of more than one material sequentially in layers so as, for example, to vary the properties of the electrode material through its thickness.

Preferably first and second electrodes are formed on an opposite surface of the substrate to the external electrical contact means. Alternatively, the first and second electrodes and the external electrical contact means, may be formed on the same side of the substrate.

The substrate may be bonded to the housing using adhesive. Alternatively, a mechanical means such as a snap-link may be used. It is preferred, however, to employ heat and/or pressure to bond the substrate to the housing. The housing preferably comprises a synthetic plastics material with a lower melting point than the substrate. When the substrate and the housing are fixed together using heat and/or pressure, housing material impregnates the substrate thereby forming a strong mechanical bond which is also impervious to the electrolyte.

A cap member having a diffusion barrier may also be provided. The substrate is positioned between the cap member and the housing. Heat and/or pressure (or other suitable method) is then applied to seal the sensor assembly. If a cap member is not used, then the permeability of at least one region of the substrate may be to modified in order to control the amount of gas reaching the electrodes, This may be achieved by use of a material with the required porosity, or the porosity may be decreased either by i) compressing the region, or ii) by impregnating the region(s) with, for example, wax, polymer, or a wax/polymer mix.

According to a further aspect of the invention there is provided a gas sensor comprising: at least first and second electrodes formed on a planar substrate; a housing containing a reservoir which, in use, contains liquid electrolyte for contacting the first and second electrodes; an electrical contact for making external electrical connection from the gas sensor; and a conductive material disposed between an electrode and the external electrical contact, wherein at least a portion of the electrode and a portion of the substrate substantially adjacent thereto, is impregnated with the conductive material, the material forming an electrical pathway through the membrane which connects at least an electrode to the external electrical contact.

The electrodes are preferably porous planar elements. The first electrode is preferably a gas sensing (working electrode) for creating the desired electrochemical reaction between the electrolyte and the gas to be sensed. The second electrode is preferably a counter electrode which performs the counterpart electrochemical reaction with oxygen. The gas sensor may include further electrodes, such as a reference electrode and/or a test gas generating electrode.

The conductive material may be in the form of a plug, pin, or other shaped component suitable for forming an electrical path between the electrodes and an external connection means.

The external electrical contact or connection means is preferably a porous planar element which may be formed on the substrate in an identical manner to the formation of the electrodes. Alternatively, the external connection means may be formed from the same, or a similar material, to the conductive material. The external connection means may also be a metal strip, or wire, which is attached to the substrate.

The sensor may have a cap so that the substrate is disposed between the cap and the housing. In this particular arrangement, the substrate is preferably highly gas permeable and presents little or no barrier to diffusion of gas there through. In such an embodiment, diffusion of gas to the sensing electrode is preferably limited by a diffusion barrier located in the cap.

Alternatively, the sensor may have no cap, so that the substrate itself acts as a diffusion barrier and forms the upper part of the housing. In this case, porosity of the substrate in certain regions is preferably decreased in order to limit the amount of gas reaching the sensing electrode and/or the counter electrode. The substrate may be flexible, semi-rigid, or rigid.

Preferably the electrolyte is sulphuric acid or other suitable electrolyte.

BRIEF DESCRIPTION OF THE DRAWINGS

Embodiments of the invention, will now be described, by way of example only, and with reference to the accompanying Figures, in which.

DETAILED DESCRIPTION OF PREFERRED EMBODIMENTS OF THE INVENTION

Figure 1:
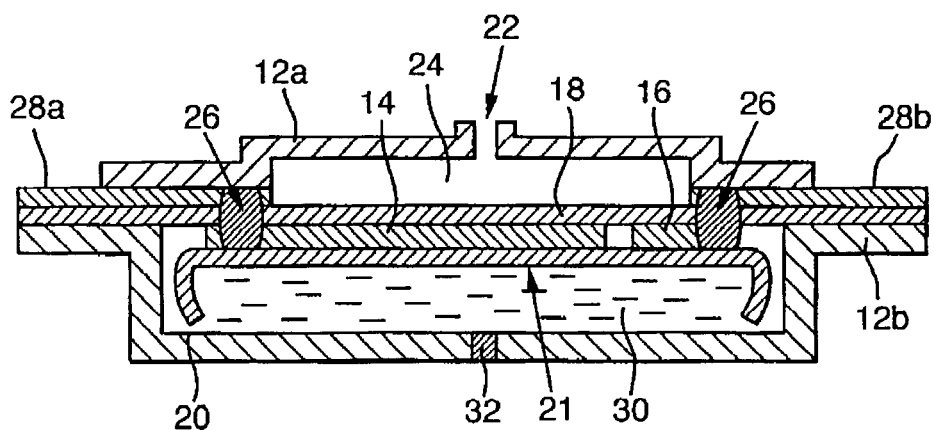
FIG. 1 shows a crass-section of a first gas sensor.

Referring to FIG. 1 there is shown a sectional view of an electrochemical gas sensor 10a in the form of a right circular cylinder, the sensor comprises a two part housing 12a and 12b, a sensing electrode 14, a counter electrode 16, and external contact tracks 28a and 28b formed on a generally circular membrane 18. Electrodes 14 and 16 are formed from a mixture of electrically conductive catalyst particles in PTFE binder, and are screen printed or filter deposited onto the surface of the membrane 18 in the form of segments, as shown in the Figure. External contacts 28a and 28b are formed by urging conductive polymer, which may be loaded with conductive non-catalytic particles, through the membrane 18.

Housing portion 12b is cylindrical with a hollow interior defining an electrolyte reservoir 20, which in use contains a liquid electrolyte 30. Electrolyte 30 is maintained in contact with the electrodes 14, 16 by means of a wick 21. The electrolyte reservoir 20 is closed at the base by means of a base member 32 having a pressure relief vent closed by a porous membrane. Housing part 12a is a disc shaped cap member having an aperture 22 therein to permit atmospheric gas to diffuse to a recessed manifold area 24, and then to sensing electrode 14. The housing portions comprise a synthetic plastics material. Aperture 22 may be in the form of a diffusion barrier to control the amount of gas reaching the sensing electrode.

Membrane 18 is disc shaped and is of approximately the same diameter as lower housing portion 12b. The membrane is disposed between upper housing portion 12a and lower housing portion 12b. As the upper housing portion 12a is smaller in diameter than lower housing portion 12b, external contact tracks 28a and 28b extend beyond the edge of upper housing portion 12a, and may thus be used as an external electrical contact or connection. The external electrical contacts may be connected to a printed circuit board and a power supply by way of pins, spring clips, or wires (not shown), A solid polymer 26 is heated and forced under pressure, through the membrane so that it forms contact 28. Details of how this is achieved are described below.

Figure 2:
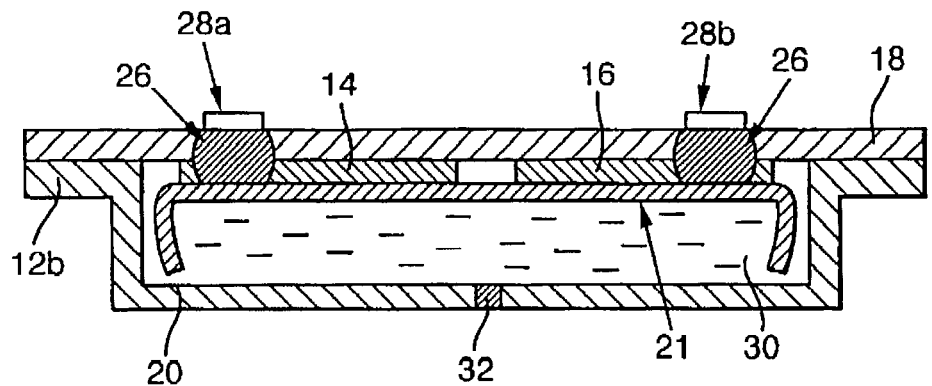
FIG. 2 shows a cross-section of a second gas sensor.

Referring now to FIG. 2 which shows a sectional view of the second embodiment 10b of the invention, similar parts to those of FIG. 1 are denoted by the same reference numerals. In this embodiment of the invention, the upper cap member 12a is not present. The membrane 18 is of a low permeability to gases in order to define a diffusion barrier for incoming gas. Thus precise control over the rate of ingress of gas is provided. The permeability of the membrane 18 may be uniform over its entire area, or the permeability may be reduced in a particular region by, for example, pressing or impregnating certain areas of the membrane with a suitable substrate.

In gas sensor 10b, regions of the electrodes 14 and 16 and the membrane 18 are impregnated with a conductive polymer 26 such that the conductive polymer 26 protrudes through the membrane 18 to form external contacts 28a and 28b. Further external electrical contact means may then be provided.

One advantage of the gas sensor according to the present invention, over existing gas sensors is that the electrodes of sensors 10a,b do not extend between the housing and the membrane 18, which are generally the weakest part of the gas sensor assembly. Thus in gas sensors 10a and 10b, a strong seal is formed between the housing and the membrane, and electrolyte is less likely to leak from the sensor.

During operation of gas sensors 10a and 10b, gas from the environment diffuses through the membrane 18 (via aperture 22 for sensor 10a) to sensing electrode 14. If this gas contains, for example, carbon monoxide, an electrochemical reaction occurs at sensing electrode 14, and an electrochemical reaction with oxygen occurs at counter electrode 16. Current is thus carried through the electrolyte 30 by ions produced in these reactions. The size of the current indicates the concentration of carbon monoxide.

A reference electrode (not shown) may be employed in combination with a potentiostat circuit (not shown) to maintain the potential between the sensing electrode 14 and the electrolyte 30 in order to increase the stability of the sensor 10a.

The assembly of sensor l0a will now be described. Electrodes 14 and 16 are formed on the lower surface of membrane 18. External contact tracks 28a and 28b are formed on the upper surface of this membrane. The wick 21 is then sintered to the electrodes 14 and 16. Molten conductive polymer 26 is introduced into required areas of the membrane 18 via holes in the wick 21, or from the upper surface of external contract tracks 28a,b, by applying heat and pressure to force the polymer through the membrane so a contact is made between external contacts 28a and 28b and electrodes 14 and 16. On solidification of the polymer 26, an electrical path is formed between the electrolyte 30 contained with electrolyte reservoir 20 and the external contact tracks 28a and 28b.

The membrane 18 is then positioned between upper 12a and lower housing portions 12b, and heat and pressure are applied using a press tool in order to compress the membrane 18 and the external contacts 28a, 28b onto the housing 12a, 12b portions, thereby bonding the assembly together. Alternatively, one or both of the housing portions 12a,b may be bonded to the membrane 18 using adhesive.

Electrolyte 30 is then introduced into the electrolyte reservoir 20 via aperture 32. This aperture 32 is then plugged with an acid-tight plug (which may be gas permeable), and sealed in place using ultrasonic bonding. This ensures that electrolyte 30 does not leak from the sensor cell 10a.

The assembly of sensor 10b is similar to that of sensor 10a. Electrodes 14 and 16 are formed on the lower surface of the membrane 18. If required, the permeability to gas of regions of the membrane 18 may be decreased, as described previously. The wick 21 is then sintered to the electrodes 14 and 16. Molten conductive polymer 26 is introduced into required areas of the membrane 18 from the upper surface of the membrane 18, by applying heat and pressure to force the material through the membrane 18 so that, on solidification, an amount solidified conductive polymer 26 protrudes through the membrane 18 to form external contacts 28a, 28b across porous membrane 18 without altering its mechanical integrity (i.e. tearing it) but provides an electrical pathway through membrane 18, to the contacts 28a, 28b. Further external contact means may be provided, held in place by the solidified conducting polymer 26.

The membrane 18 is then positioned above lower housing portion 12b, and heat and pressure are applied using a press tool in order to compress the membrane 18 onto the housing portion 12b, thereby bonding the assembly together. Alternatively, the lower housing portion 12b may be bonded to the membrane 18 using adhesive. Electrolyte 30 is then introduced into the electrolyte reservoir 20 as previously described.

Referring to FIGS. 1 and 2, a conductive contact 28a, 28b is formed by the process of impregnation of the porous membrane or substrate 18 by the conductive material in liquid form. In a preferred method, the substrate 18 is a polymeric material with open porosity, and the material to be impregnated is a polymer with lower melting point than the substrate material, loaded with conductive particles. The impregnating material 26 is forced into the pores of the substrate 18 in liquid form under pressure, so as to form a conductive mass 26 within the pores extending from one side of the substrate 18 to the other. The mean size of the conductive particles may be smaller than that of the pores in the substrate 18, or may be comparable or larger, in which case the impregnation process and the substrate material are chosen to give sufficient deformation to the pores in the substrate 18, through heat, pressure or both, to allow the conducting particles to pass through them sufficiently to produce a conductive path.

The conductive material may be introduced by a tool which leaves an amount of the material on the surface on one or both sides which is moulded by the tool (not shown), or in a subsequent process, into a desired shape, for instance to form an electrical contact 28, either to further connection means intended to pass outside the cell or to another similar conductive assembly on a further substrate. The substrate 16 may have an electrode or connector track associated with it, preferably integral with the substrate and formed on it be for example screen-printing or suction deposition.

In a preferred method, the substrate material is a porous fluoropolymer membrane, for example porous PTFE, and the impregnating material is polypropylene loaded with carbon particles. The melting point of the loaded polypropylene, less than 200° C., is significantly less than that of the PTFE (softening point around 300° C.), allowing the polypropylene to be forced through the pores of the PTFE easily by a tool temperature of typically 200–240° C.

Example: For a PTFE sheet such as Mupor (Registered Trade Mark) type 131 (MUPOR Ltd., Alness, UK), thickness 0.2 mm with mean pore diameter 2 µm, and impregnating material polypropylene loaded with 40 wt % carbon black particles of mean agglomerate dimension of order 200 nm (material from Whitaker Technical Plastics Ltd., Macclesfield, UK) good conductivity through the membrane was achieved using a hot pressing technique, at 200–240° C., and a pressure of approximately 200 N/cm$^2$, for 10 s. This produced a low resistance contact through the membrane to a Pt/PTFE gas diffusion electrode, which was porous with mean pore size similar to that of the membrane, mounted on the opposite side of the membrane. Such an electrode and contact could be used in a gas sensor as shown in the embodiments described, to detect carbon monoxide.

Figure 3:
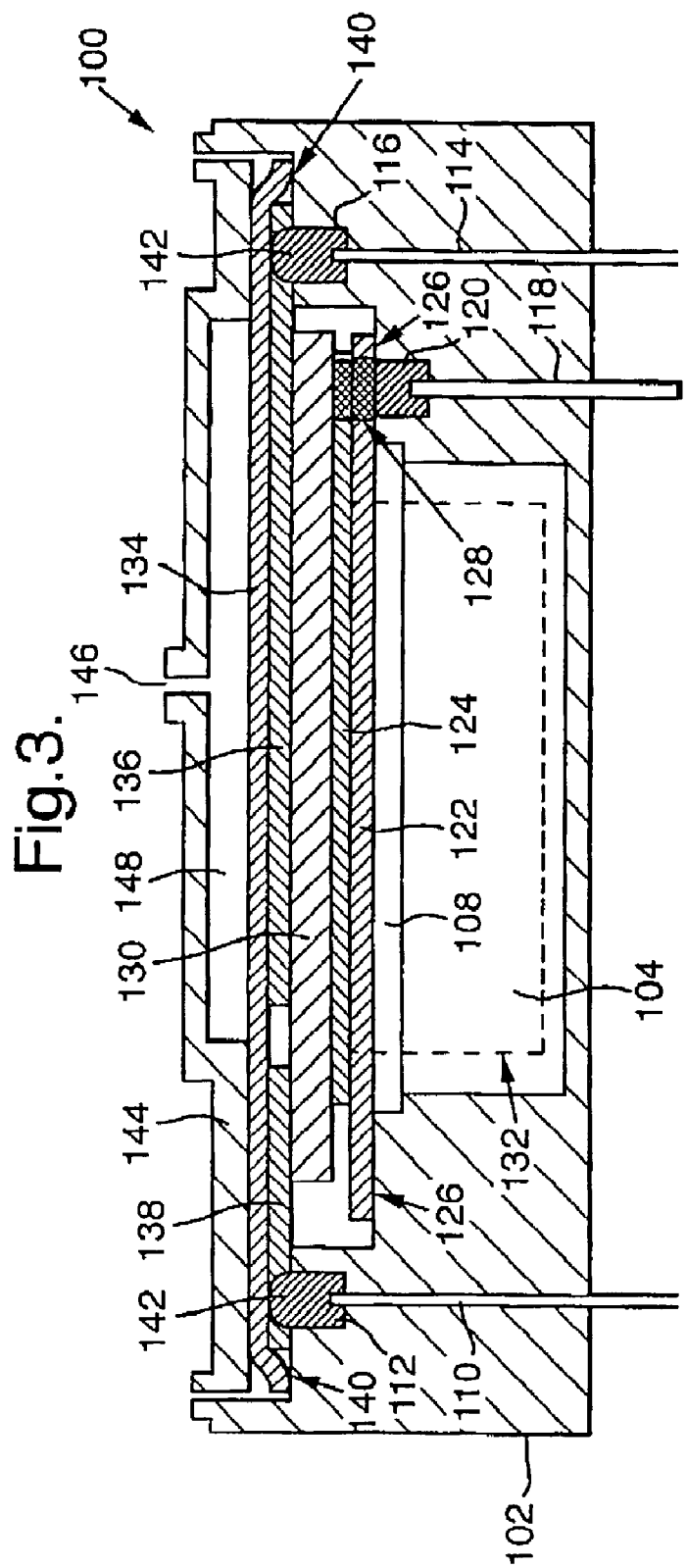
FIG. 3 shows a sectional view through another gas sensor.

FIG. 3 shows a gas sensor 100 comprises a housing 102 with a reservoir 104 for liquid electrolyte. The reservoir 104 has at its upper end a support member 108 mounted on or attached to the housing 102 to provide a rigid or semi-rigid support for the components connected thereto. The housing 102 has mounted in it contact pins 110, 114, 118 each in good electrical contact with associated moulded components of conducting polymer 112, 116, 120. Overlying the support member 108 is a first electrode assembly consisting of a porous substrate 122 with a catalyst layer 124. The catalyst material is preferably sintered together with the electrode to produce a robust electrode assembly. The catalyst layer (or electrode 124) is formed on the substrate 122 prior to introducing the substrate 122 into the housing 102, by for example screen-printing, suction deposition etc. The catalyst layer 124 might be a porous layer formed from a catalytic material such as Pt or Ru02, bound together and to the substrate 122 by means of a PTFE binder as is known in the art. Alternatively it might be a nonporous material, for example a metal film, possibly treated to increase its catalytic activity. The substrate 122 is porous and is of a material of higher melting point than the material of the housing 102 and the conducting polymer 120.

The electrode assembly is sealed into the housing 102 with catalyst layer 124 uppermost as shown, by for example application of heat and pressure, or ultrasonic welding. The housing 102 material is locally melted and forced into the porous substrate 122 forming a strong bond in the bonding regions 126. Simultaneously, the conducting polymer 120, which initially projects above the level of the housing 102 surrounding it, melts and is forced through the substrate 122 and into contact with the catalyst 124. If the catalyst 124 is porous, then the conducting polymer 120 is preferably forced into the catalyst layer 124, so improving the electrical contact and physical robustness of the assembly.

A wick assembly 130 overlies the first catalyst 124. The wick assembly 130 is compressible and has extensions (shown as dotted outline 132) which reach down into the electrolyte reservoir 104. As second electrode assembly, consisting of one or more electrodes—two are shown in FIG. 3, as 136 and 138—on a second porous substrate 134, contacts the wick 130 on the opposite side. At least the second electrode 136 consists of a porous catalytic layer capable of reacting signal gas in the presence of air and electrolyte.

The second electrode assembly is sealed to the housing 102 with the second electrode 136 lowermost, by application of heat and pressure, ultrasonic welding or similar means as before. The housing material is forced into the substrate 134 forming a bond in the bonding regions 140 and the conducting polymer 112, 116 is melted and impregnated into the electrode 136, 138 and any other electrode that is provided on the common substrate 134 according to details of the embodiment, making electrical contact with them. This second process of sealing and making contact is essentially as described in the Applicant's granted US patent U.S. Pat. No. 5,914,019. Finally a housing cap 144 is mounted onto the housing 102, by heat sealing, ultrasonic welding or the like. Cap 144 provides access of gas from the exterior to the electrode 136 via the porous substrate 134 and a gas distribution space 148, that access being limited by a diffusion barrier 146, shown in the form of a capillary. The reservoir 104 is partially filled with electrolyte (typically sulphuric acid) via a filling plug in the housing (not shown).

In use, second electrode 136 with gas access from the exterior, acts as the sensing electrode, and first electrode 124 acts as a reference electrode or in a two electrode cell, the counter electrode. If a third electrode 138 is provided, then this acts as the counter electrode.

Variations may be made, for example, the first substrate 122 might have two electrodes on it, with a second conducting polymer and pin contact arrangement to make contact to it, these electrodes functioning as the counter and the reference electrodes, and the second substrate 134 might have just one.

While the contact arrangements 114, 116 and 118, 120 are shown as being at different distances from the edge of the cell, these might be located in any practical geometry as suits the sealing process and tooling, for example, they might be in line with one another relative to the edge. Also, while the bonding regions 126 and 140 are shown as being at different levels in the cell, and the seal processes have been described as being done in two stages, especially if very thin components are used these surfaces might be at the same level, with compliance and flexibility of the components optionally being exploited to allow the seals to be made simultaneously.

The contacts are shown as being formed by a contact pin joined to the electrodes by a conductive polymer mass; alternatively, the pin might be absent and the conductive polymer might itself lead to the outside of the cell, either with the conductive polymer co-moulded as part of the housing, or it may be bonded to the housing a separate components after moulding.

A further variation on this embodiment is in the design of the support means, shown as the support member 108. This could instead comprise a compliant component compressed between the base of the reservoir and the underside of membrane 122, with optional further sheet components to give even support to the components above it.

The stacked construction employed in the present invention reduces area used on the common substrate so reducing the "footprint" of the cell; secondly, in planar designs such as that in U.S. Pat. No. 5,914,019 steps must be taken to prevent signal gas from reaching the reference electrode—this implies some form of seal between the edge of the gas distribution space 148 and the reference electrode. This seal is a source of unreliability and it is a great advantage to avoid need for it. The positioning of the reference electrode on the other side of a wick from the sensing electrode prevents signal gas from reaching it as (i) gas cannot diffuse quickly through the wick and (ii) most if not all signal gas will have reacted at the sensing electrode anyway.

Variation may be made to the aforementioned embodiments without departing from the scope of the invention. For example, for the sensors described herein, three or more electrodes may be formed on the membrane. These additional electrodes may generate a test gas so that the sensors have self-test capability.

What is claimed is:

1. A method of manufacturing a gas sensor comprising:
   a. providing a housing containing a reservoir;
   b. receiving an electrolyte in the reservoir;
   c. impregnating a substrate of a gas porous membrane with a conductive material, so that said conductive material defines an electrical pathway between an electrical contact on a first surface of the membrane and an electrode on a second surface of the membrane; and
   d. arranging the membrane to seal the reservoir,
      wherein the substrate of the gas porous membrane is impregnated with the conductive material via a wick.

2. A method according to claim 1 further including the step of attaching the wick to the electrode.

3. A method according to claim 2 whereby the wick is pressed or sintered to the electrode.

4. A method according to claim 3 whereby the wick is sintered to the electrode at a temperature of between 300° C. and 370° C.

5. A method according to claim 3 whereby the wick is sintered to the electrode at a temperature of between 320° C. and 370° C.

6. A method according to claim 1 whereby the gas porous membrane is impregnated by the conductive material via the electrode.

7. A method according to claim 1 whereby gas porous membrane is impregnated by the conductive material in a melted state.

8. A method according to claim 1 whereby the electrode and the electrical contact are formed on the gas porous membrane by any one of the following:
   (a) screen printing;
   (b) filtering in selected areas from a suspension placed onto the gas porous membrane; or
   (c) spray coating.

9. A method according to claim 1 wherein the gas porous membrane and the housing are bonded together using adhesive.

10. A method according to claim 1 wherein the gas porous membrane and the housing are bonded using heat and/or pressure so that a material forming the housing melts and impregnates the gas porous membrane, thus forming a strong bond therebetween.

11. A method according to claim 1 whereby the permeability of at least one region of the gas porous membrane to gas is decreased in order to limit the amount of gas reaching the electrode.

12. A method according to claim 11 whereby the permeability of at least one region of the gas porous membrane to gas is decreased by any one or combination of the following steps:
   a) compressing the region;
   b) impregnating the regions with wax; or
   c) impregnating the region with a polymer.

13. A gas sensor comprising:
   a. an electrode formed on a gas porous membrane;
   b. a housing containing a reservoir, wherein when in use, the reservoir contains a liquid electrolyte for contacting the electrode;
   c. an electrical contact, configured to make an external connection from the gas sensor;
   d. a conductive material disposed between the electrode and the electrical contact; and
   e. a wick being arranged to contact both the liquid electrolyte and the electrode, the wick having at least one aperture formed therein through which the conductive material can be introduced,
      wherein at least a portion of the electrode and a portion of the gas porous membrane substantially adjacent thereto, are impregnated with the conductive material, the conductive material forming an electrical pathway through the gas porous membrane which connects at least the electrode to the electrical contact.

14. A gas sensor according to claim 13 wherein the electrode and/or the electrical contact are formed from a porous electrically conductive material containing a catalyst material.

15. A gas sensor according to claim 13 wherein the electrode is a sensing electrode for creating the desired electrochemical reaction between the electrolyte and a gas to be sensed.

16. A gas sensor according to claim 13 wherein the electrode is a counter electrode which performs an electrochemical reaction with oxygen.

17. A gas sensor according to claim 13 further including a reference electrode.

18. A gas sensor according to claim 13 further including a gas generating electrode.

19. A gas sensor according to claim 13 wherein the conductive material includes a conductive polymer.

20. A gas sensor according to claim 19 wherein the conductive material is a plug, pin, or other shaped component suitable for forming an electrical path between the electrode and the electrical contact.

21. A gas sensor according to claim 13 wherein the electrical contact includes a conductive polymer.

22. A gas sensor according to claim 13 wherein the electrical contact is a metal strip attached to the gas porous membrane.

23. A method of forming an electrical pathway across a microporous membrane having first and second major surfaces, where the microporous membrane is impervious to liquid and permeable to gas, comprising the steps of:
   a.) maintaining sufficient heat to melt a conductive material;
   b.) urging the melted conductive material through pores of the microporous membrane at a first surface by establishing a pressure differential across the first and second surfaces;
   c.) controlling the heat and pressure differential until the melted conductive material emerges at the second surface; and
   d.) allowing the material to cool so as to form a continuous, electrically conductive pathway from the first surface to the second surface while preserving the liquid impermeability and gas permeability characteristics of the microporous membrane.

* * * * *